(12) United States Patent
Jenkins, III

(10) Patent No.: US 12,029,413 B2
(45) Date of Patent: Jul. 9, 2024

(54) KNOTLESS SUTURES AND ANCHORING CLIP FOR KNOTLESS SUTURES

(71) Applicant: Jenkins Neurospine LLC, New York, NY (US)

(72) Inventor: Arthur L. Jenkins, III, Old Greenwich, CT (US)

(73) Assignee: Neurotect LLC, Greeniwch, CT (US)

( * ) Notice: Subject to any disclaimer, the term of this patent is extended or adjusted under 35 U.S.C. 154(b) by 541 days.

(21) Appl. No.: 16/946,667

(22) Filed: Jun. 30, 2020

(65) Prior Publication Data

US 2021/0401426 A1    Dec. 30, 2021

(51) Int. Cl.
*A61B 17/04*    (2006.01)

(52) U.S. Cl.
CPC ...... *A61B 17/0487* (2013.01); *A61B 17/0401* (2013.01); *A61B 2017/0409* (2013.01); *A61B 2017/0446* (2013.01)

(58) Field of Classification Search
CPC . A61B 17/0401; A61B 17/0487; A61B 17/06; A61B 2017/0446; A61B 2017/0448; A61B 2017/0454; A61B 2017/06052
See application file for complete search history.

(56) References Cited

U.S. PATENT DOCUMENTS

| | | | |
|---|---|---|---|
| 4,950,285 A * | 8/1990 | Wilk | A61B 17/06 24/17 AP |
| 5,545,190 A | 8/1996 | Le et al. | |
| 6,024,758 A | 2/2000 | Thal | |
| 2004/0122456 A1 | 6/2004 | Saadat et al. | |
| 2006/0064125 A1 | 3/2006 | Henderson et al. | |
| 2010/0256676 A1* | 10/2010 | Hay | A61B 17/0487 606/232 |
| 2013/0110165 A1 | 5/2013 | Burkhart et al. | |
| 2018/0221133 A1 | 8/2018 | Lund | |

FOREIGN PATENT DOCUMENTS

| | | |
|---|---|---|
| WO | 2013034644 A1 | 3/2013 |
| WO | 2020111610 A1 | 6/2020 |

OTHER PUBLICATIONS

International Search Report and The Written Opinion on the International Searching Authority PCT/US21/39770 for Knotless Sutures and Anchoring Clip for Knotless Sutures This document is relevant because it was issued in a PCT case related to the pending case.

* cited by examiner

*Primary Examiner* — Todd J Scherbel
(74) *Attorney, Agent, or Firm* — Welsh IP Law LLC

(57) ABSTRACT

A system for securing a suture to a wound, durotomy, or other hole. A first anchor is anchored against an insertion point and a suture thread is passed through a loop on the first anchor. The wound is then stitched. A second anchor at an end of the wound holds the other end of the suture thread, to keep the tension in the suture. The suture thread is connected to the second anchor via clipping.

19 Claims, 4 Drawing Sheets

ND ANCHORING
KNOTLESS SUTURES AND ANCHORING CLIP FOR KNOTLESS SUTURES

TECHNICAL FIELD

The present invention relates to a system of knotlessly securing of a suture to a wound, durotomy, or other hole. The system includes a first suture anchor of a distal end of the suture, having a loop, and a second suture anchor placed at the proximal end of the wound, which anchors the proximal end of the suture thread.

BACKGROUND

For surgical or other large wounds, there exists a technique of closing the wound via sutures which allow the tissue and skin to heal together at a faster pace than if left alone. As the suture is stitched around the edge of a wound, it can be tensioned such that the edges of the wound are joined together. Typically, the sutures have been tensioned by applying a suture anchor on an insertion point at one end of the wound, to keep the start of the suture in place. After the wound has been stitched, tying a knot at the end of the wound helps keep the tension throughout the suture. Alternatively, it is possible to tie a knot after each stitch to keep tension throughout the suture thread. Knots, however, are time consuming to tie and untie, difficult to do during a surgical procedure, and if done in a deep wound are potentially dangerous.

Knotless tissue anchors are used in surgical procedures to start a suture line. For example, EP 0910287 describes a knotless suture anchor to repair detached soft tissue. Knotless tissue anchors, as commonly defined, do not require the tying of knots by a user (e.g., surgeon) to secure the tissue at the insertion point. Instead, the anchor has a locking feature which secures the suture, and thus the tissue. The locking points are often pin shaped and dig into skin or bone to keep the suture in place. Such anchors have grown in popularity due to their ease of use and simplification of the surgical procedure by, for example, eliminating the need for knot pusher instruments and the like. Nevertheless, there is a need for a knotless suture anchor that does not require penetration, while still maintaining the security of the suture.

Despite having knotless anchors, methods of applying the suture still require knots to be tied at the proximal end of a wound. After being anchored at a distal end, sutures are tied with a knot at the proximal end to keep the tension throughout the entire suture thread or tied in a knot at each stitch. Otherwise, the suture, and thus the wound, would come loose.

Due to human error, the knots tied by a surgeon, or other user, are not equal in force or neatness. Knots are time-consuming and complicated for implementation and removal. Therefore, a system to anchor and tension a suture without tying a knot at either end is beneficial.

Thus, there exists a need in the art for an improved method of applying a suture to a wound which can be done in a simplified and time-saving way without causing excessive risk of harm or discomfort to a surgical patient.

SUMMARY

The needs set forth herein as well as further and other needs and advantages are addressed by the present teachings, which illustrate solutions and advantages described below.

It is an objective of the present invention to create a secure suture attachment without the need to penetrate the skin, bone, or other tissue and still secure the suture in place. This may be accomplished by a suture thread having a loop on an end opposite a needle, having an anchor near the loop end. The anchor may be made out of the same material as the rest of the suture. In one object of the invention the anchor may be made from the same piece of that material as the rest of the suture.

The anchor may be umbrella shaped to keep tension in the suture. After the needle is passed through the skin or tissue for a first time, it is fed through the loop and pulled taut. This creates a slipknot, and keeps the needle tensioned on a plane of the wound. As the suture is pulled taut, a force is pulled down on the umbrella shaped anchor, flattening it against the surface of the wound. The flatness of the anchor may cause a suction force beneath it and may also cause additional friction between the suture and the tissue.

It is an objective of the present invention to allow the user to clip the suture in a speedy and sufficient manner. When a wound is created either through an accident, surgery, or other means, prompt and efficient correction of the wound is beneficial to the patient. During surgery the wound that needs to be stitched may be deep in the patient, and thus a simpler method than tying knots is beneficial to reduce the time the wound is laid open and also requires less dexterity by the user (e.g. surgeon) thus leaving less room for error.

An object of the present invention is completed using a first anchor placed at a distal end of a wound. The first anchor has a suture thread and a tensioning means to keep the suture taut at the distal end. A second anchor is placed at a proximal end of the wound. After stitching the suture through the wound, as appropriate, the suture is affixed to the second anchor to keep the suture taut at the proximal end.

The suture can be made from any material, for example, Vicryl™, Nylon™, or silk. The stitching end of the suture may have a needle or be affixed to a needle. The needle may help the user stitch through the skin or other material in order to close the wound. The suture is also connected to the first anchor. In one object of the invention the suture comprises the anchor on its end opposite the needle.

The anchor is any device which secures the suture to the soft or hard tissue. In one object of the invention the anchor is a pledget. The pledget may be laid across the entire wound, partially over the wound, or only at the beginning. If the pledget is laid across the entire wound, it may be laid under the second anchor at the distal end of the wound.

The second anchor and the first anchor may be different. In an object of the invention the second anchor may be a clip, such as a hemoclip. The clip can be gently pushed to the edge of the tissue to maintain tension on the rest of the suture thread.

In another object of the invention the second anchor may be tented while unsecured to allow the suture to pass through it. When the suture is passed through the anchor, the anchor may be clipped shut to secure the suture within the anchor. The act of clipping may cause the suture to lie flat against the surface of the wound.

In another object of the invention, the suture can be stitched through the wound and then passed through a second anchor at the proximal end of the wound. The second anchor may have flanges, through which the suture can be threaded. A clip can seal the flanges with the suture between the flanges. Alternatively, the suture can be pulled taut between the flanges until the anchor rests neatly against the skin or surface, and then the clip will seal the flanges together. Pushing the clip to the edge of the skin or surface will also maintain tension on the remainder of the suture line which is beneficial to healing the wound and keeping the suture line in place.

After the suture is anchored at the distal end, stitched through the wound, and then anchored at the proximal end, the remainder of the suture can be cut. The cut can be very close to the clip or allow excess thread in case of slippage or adjustment in the thread tension.

Other features and aspects of the invention will become apparent from the following detailed description, taken in conjunction with the accompanying drawings, which illustrate by way of example the features in accordance with embodiments of the invention. The summary is not intended to limit the scope of the invention, which is defined solely by the claims attached thereto.

BRIEF DESCRIPTION OF THE DRAWINGS

It should be understood that through the drawings, corresponding reference numerals indicate like or corresponding parts and features.

DETAILED DESCRIPTION

The present teachings are described more fully hereinafter with reference to the accompanying drawings, in which the present embodiments are shown. The following description illustrates the present teachings by way of example, not by way of limitation of the principles of the present teachings.

The present teachings have been described in a language more or less specific as to structural features. It is to be understood, however, that the present teachings are not limited to the specific features shown and described, since the device herein disclosed comprised preferred forms of putting the present teachings into effect.

Figure 1:
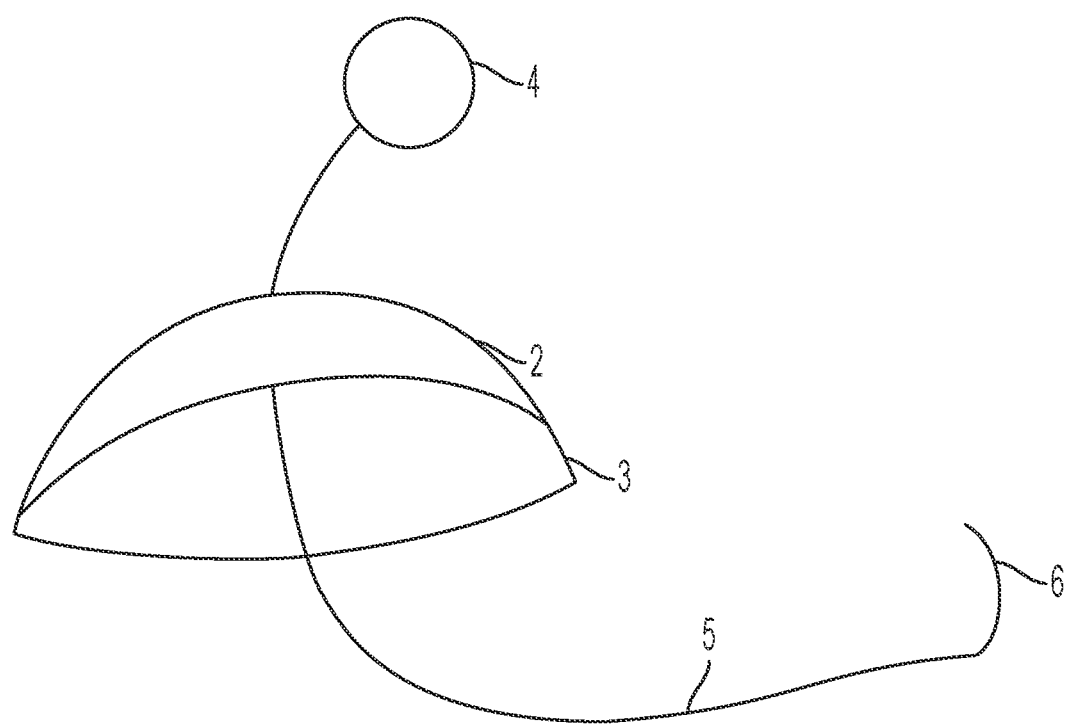
FIG. 1 is an isometric view of a knotless suture.

FIG. 1 depicts a suture having an anchor 2. The anchor 2 has a bottom surface 3. On one end of the suture thread 5 is a loop 4 and on the other end of the suture is a needle or other point 6. The anchor 2 is shown The anchor 2 may come in many shapes. The anchor can be shaped like an umbrella, as in FIG. 1. The anchor may also be shaped as a flat circle, cylindrical, pyramidal, or as other 2 and 3 dimensional shapes. This allows the anchor to rest snugly against a surface of the wound, or other tissue surface to be stitched.

The suture thread 5 is affixed to the suture anchor 1. In some cases, the suture thread 5 may be permanently affixed to the suture anchor 1. In other objects of the invention the suture may be attached to the anchor using a variety of non-permanent methods such as a knot, glue, clamping, or other methods appreciated by those skilled in the art. In other objects of the invention, the suture thread 5 may be continuous with the anchor 2. For example, if the suture thread 5 and the anchor were formed from the same piece of starting material. The end of the suture thread 6 may comprise a needle. A needle would help with stitching the suture thread 5 through thicker material such as skin or a pledget.

In other objects of the invention, the suture thread 5 may have various features (not shown). The features may be angled spikes or other features as appreciated by those skilled in the art. The features are beneficial to aid in preventing the suture thread from being pulled backwards.

Figure 2:
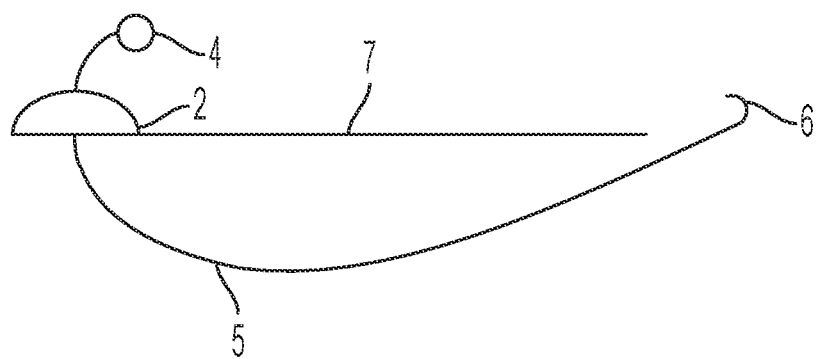
FIG. 2 is a side view of a suture in a wound.

FIG. 2 shows the system for applying a suture where the suture has run through the surface 7. The suture thread 5 may be pulled taut towards the proximal direction of the surface 7 (away from the first anchor) to move the anchor 2 into place. By first pulling the suture thread 5 taut, it will tug at the anchor 2 from the center. This force will draw the anchor closer to the surface 7.

The surface 7 may be the skin of a patient where a wound has formed. The surface 7 may also soft tissue, hard tissue, a pledget, bone, or any other surface as appreciated by one skilled in the art, including those unrelated to the medical profession. One skilled in the art would understand that the surface 7 may be and internal surface inside the body, such as a spinal column.

Once the suture thread 5 is taut against the surface 7, the suture thread 5 can be stitched through the surface 7. For example, the suture thread 5 can be stitched through a wound in skin. While a wound generally refers to a medical patient, one skilled in the art would understand that any hole or deformity in a surface 7 may be considered a wound.

Figure 3:
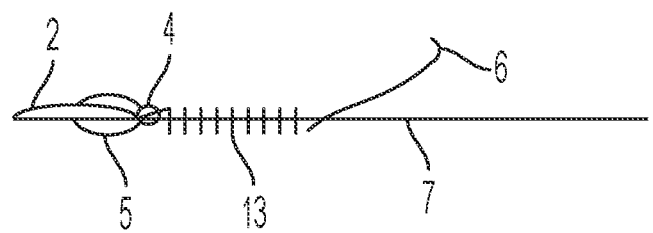
FIG. 3 is a side view of a suture stitched in a wound.

FIG. 3 depicts the suture anchor 2 pulled almost flat against the surface 7, as the wound is stitched by suture thread 5. Stitches 13 are made in the wound to help seal it shut. The suture thread 5 has been passed through the loop 4 creating a slipknot. The slipknot tensions the suture thread 5 at the beginning of the wound.

The loop 4 has a portion of the suture thread above the anchor 2. This portion of the suture thread may be the exact length of the radius of the suture anchor 2 when flat. In other objects of the invention the length of suture thread 5 before the loop 4 is slightly longer than the radius of the suture anchor 2. The length of thread before the loop 4 may also be relative to the radius of the suture anchor 2 at a certain degree of flatness.

Figure 4:
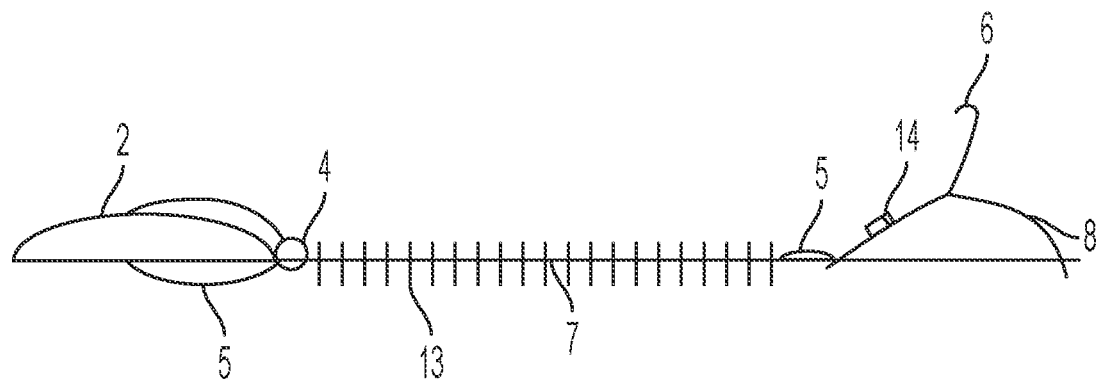
FIG. 4 is a side view of a system for knotlessly anchoring a suture.

FIG. 4 depicts a system to keep the suture thread 5 tensioned at both ends of the wound. It is important to keep tension in the suture thread 5 as the tension may keep the sides of the wound connected, allowing tissue to heal or creating a better seal.

FIG. 4 further depicts a second anchor 8 at the proximal end of the wound. The second anchor may be placed before or after the stitching has been completed. The suture thread 5 is then fed through the second anchor 8. The anchor 8 may have flanges which stick out from the surface of the anchor 8, between which the suture thread may be run.

A clip 11 may be used to secure the suture thread 5 to the anchor 8. The clip 11 may be connected at any height of the anchor 8 of the anchor. Optionally, after connection, the clip 11 can be moved until it rests partially against the surface 7. This would allow the suture thread 5 to keep maximum tension over the wound. The clip may also be connected to the flanges 14. The flanges 14 would allow a surface for the clip to grip, such that when the flanges are clipped together, the anchor would completely shut.

The objective of the invention can also be completed where the clip 11 is the anchor 8. Here, after the suture thread 5 is stitched through the wound, the clip 11 is applied to the suture thread 5 against the surface 7. The clip may stay in position via an adhesive, clipping the surface relying on friction, or any other method appreciated by one skilled in the art.

The anchor 8 may also be a pledget or pledget-like material. The pledget could seal the suture thread 5 beneath it or the clip 11 could clamp the suture thread 5 through the pledget. Further, if a pledget is used across the entire wound, both the first anchor 2 and second anchor 8 could be the same pledget. A pledget is a suitable material for an anchor because it is both soft enough to be deformed by the clip, but also rubbery enough to grip the suture it is clipped to. It is also within the scope of the invention to electrically, thermally, or chemically bond the clip to the suture. This would prevent the clip from slipping along the suture thread.

The anchor 8 may be shaped as a circular sector having a reflex angle. When the suture thread 5 has finished stitching the wound 12, the thread would be placed through the open portion of the circular sector, and the anchor 8 would then be closed such that the suture thread 5 is sealed between the flat sides of the circular sector. As appreciated by one skilled in the art, the anchor 8 may be in many different shapes and a circular outer shape is only one plausible embodiment. The anchor 8 may also start raised, such that it is shaped as a cone having a circular sector base. The flanges 14 may stick off the straight edges of the pyramid. If a clip seals the flanges 14, the anchor 8 would flatten against the surface 7. The suture thread may be led such that it sticks out the center of the anchor 8. In other objects of the invention, the anchor 8 may be shaped different. For example, the base may be an elliptical sector such that when the flanges 14 are clipped together the anchor 8 forms a flat circle.

A clip may resemble a hemoclip, be custom-designed to form an anchor, or have any other form as appreciated by one skilled in the art. The anchor 8 may also comprise the clip within its structure. Clips to be applied to the anchor 8 or suture thread 5 may be too small to apply with human hands. Therefore, it may be necessary to apply clips with an applier.

Figure 5:
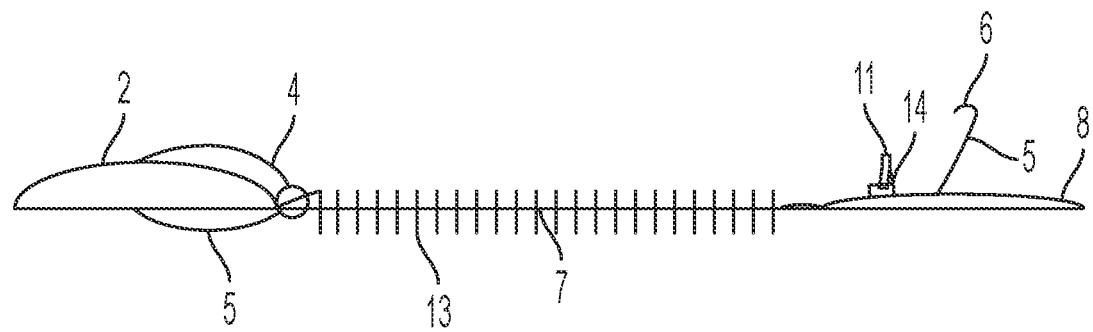
FIG. 5 is a side view of a system for knotlessly anchoring a suture.

FIG. 5 shows a system for knotlessly anchoring a suture. The suture thread 5 has been stitched through the surface 7 of a wound. The stitches 13 hold the wound in place to allow healing. The first anchor 2 is pulled by suture thread 5 against the surface. A slipknot between the loop 4 and the suture thread 5 keeps tension at the distal end of the wound. On the proximal end of the wound a second anchor 8 is almost flat against the surface 7. The needle 6 is attached to the suture thread 5 coming out the center of the second anchor 8. The clip 11 has sealed the flanges 14 together, so the suture thread is tensioned against the second anchor 8. Therefore, the suture thread 5 is tensioned at the distal and proximal ends without the need to tying a knot.

Figure 6:
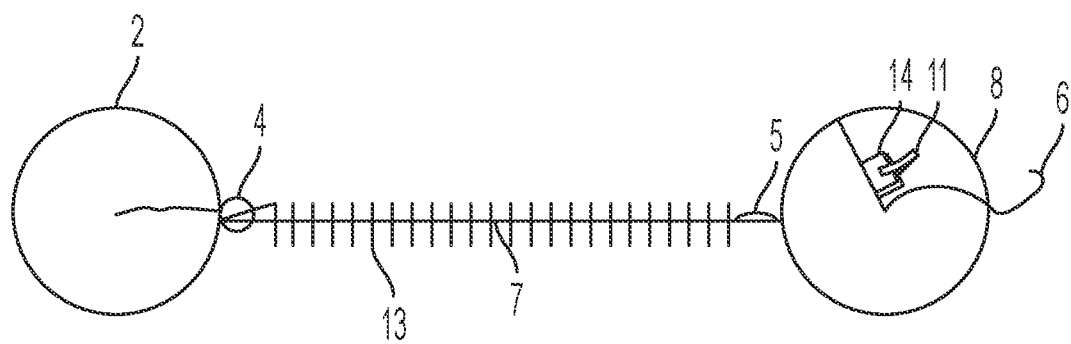
FIG. 6 is a top down view of a system for knotlessly anchoring a suture.

FIG. 6 shows a top-down view of the system for knotless tensioning a suture thread 5, as shown in FIG. 5. Once the suture thread 5 is secured in the second anchor 8, the needle 6 and excess thread may be cut off. The cut may be done very close to the clip 11 or closer to the needle 6 depending on the user's preference.

In one object of the invention, the clip 11 may be redundant and unnecessary if the anchor 8 can clip the suture thread 5 without an external clip.

It should be understood to a person of ordinary skill in the art that different configurations of the system for anchoring a suture are possible. For example, the design layout of the anchored suture may differ from those shown in the Figures without departing from the scope and spirit of the present teachings.

While the present teachings have been described above in terms of specific embodiments, it is to be understood that they are not limited to those disclosed embodiments. Many modifications and other embodiments will come to mind to those killed in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. A knotless suture comprising:
   a loop at a distal end of the suture, the loop having a greatest opening D being the longest line that can be drawn across the loop while still touching two points on the loop;
   an anchor configured to fix the knotless suture relative to a wound in a tissue, the anchor defining a cross section transverse to a longitudinal axis of a first thread connecting the loop to a first side of the anchor, the anchor configured to abut against a surface of the wound, the cross section having a greatest width W;
   a needle at a proximal end of the suture;
   a second thread connecting the needle to a second side of the anchor;
   wherein W is greater than D.

2. The knotless suture of claim 1 wherein the loop, the first thread, and the second thread are all made of the same material.

3. The knotless suture of claim 2 wherein the loop, the first thread, and the second thread are all made of a continuous piece of the same material.

4. The knotless suture of claim 1 wherein the anchor is an umbrella shape.

5. The knotless suture of claim 4 the first thread is substantially the same length as a radius of the anchor.

6. The knotless suture of claim 5 wherein when the second thread is pulled through the loop a slipknot is created wherein when the slipknot is taut the anchor is flattened against the surface of the wound.

7. The knotless suture of claim 4 wherein the first thread plus the diameter of the loop are substantially the same length as the radius of the anchor.

8. The knotless suture of claim 1 wherein the second thread has a plurality of features.

9. A system for knotlessly securing a suture to a wound comprising:
   a suture comprising:
      a first anchor;
      a loop at a distal end of the suture;
      a thread beginning at the anchor, on the opposite side of the loop; and
   a needle at a proximal end of the suture;
   a second anchor having flanges;
   a clip capable of clamping the flanges together;
   wherein after the wound is stitched by the suture, the thread is led through the center of the second anchor such that when the clip is applied to the flanges, the suture is kept taut by the second anchor.

10. The system of claim 9 wherein the first anchor, loop, and thread are all made of a continuous piece of the same material.

11. The system of claim 9 wherein the second anchor is shaped as a cone, the cone's base being a circular or elliptical sector having a reflex angle.

12. The system of claim 11 wherein when the clip clamps the flanges together the second anchor lies flat against a surface of the wound.

13. The system of claim 9 wherein the loop is connected to the first anchor via a loop thread, wherein the loop thread is substantially the same length as the radius of the first anchor.

14. The system of claim 9 wherein the second anchor is a pledget.

15. A suture anchor comprising:
   an elliptical sector outer rim having a reflex angle;
   two flanges, one on each radial edge of the elliptical sector;
   a clip capable of clamping the flanges together; and
   wherein in an unclipped state the anchor is shaped as a cone with a sector missing and when in a clipped state the anchor is shaped as an ellipse or a cone, wherein in the clipped state, the anchor having a height smaller than the cone, the cone in the unclipped state.

16. The suture anchor of claim 15 wherein the suture anchor is a pledget, or pledget-like material.

17. The suture anchor of claim 15 wherein a suture thread is configured to run radially between a surface of a wound and the anchor and exits through the center of the anchor.

18. The suture anchor of claim 15 wherein the clip is applied to the flanges with an applier.

19. The suture anchor of claim 15 wherein the clip is attached to the anchor electrically, thermally, or via chemical bond.

\* \* \* \* \*